United States Patent [19]

Bardy et al.

[11] 3,931,396

[45] Jan. 6, 1976

[54] METHOD OF PREPARATION OF A COMPOSITION HAVING A BASE OF $99^M$ TECHNETIUM FOR DIAGNOSIS BY SCINTIGRAPHY

[75] Inventors: André Bardy, Morangis; Jacqueline Beydon, Paris, both of France

[73] Assignee: Commissariat a l'Energie Atomique, Paris, France

[22] Filed: Mar. 26, 1974

[21] Appl. No.: 455,005

Related U.S. Application Data

[63] Continuation-in-part of Ser. No. 365,695, May 31, 1973, abandoned.

[52] U.S. Cl.................. 424/1; 23/230 B; 206/84; 250/303; 424/128
[51] Int. Cl............................................. A61k 27/04
[58] Field of Search ......................... 424/1

[56] References Cited
OTHER PUBLICATIONS

Subramanian et al., Radiology, Vol. 99, No. 1, pp. 192 to 196, (Apr. 1971).

*Primary Examiner*—Leland A. Sebastian
*Attorney, Agent, or Firm*—Lane, Aitken, Dunner & Ziems

[57] ABSTRACT

A method for preparing a pyrophosphate-tin composition labelled with $99^m$ technetium for medical diagnosis by scintigraphy, especially bone scintigraphy. A pyrophosphate solution and a freshly prepared stannous chloride solution are mixed together and then neutralized to a pH within the range of 5 to 7, the mixture is eventually lyophilized in order to obtain a pyrophosphate-tin complex in powder form which is then mixed with a solution containing $99^m$ Tc, the last-mentioned final step of the method being carried out at the moment of use. The complex has a pyrophosphate-tin molecular ratio of at least 30.

7 Claims, No Drawings

METHOD OF PREPARATION OF A COMPOSITION HAVING A BASE OF 99$^M$ TECHNETIUM FOR DIAGNOSIS BY SCINTIGRAPHY

CROSS-REFERENCE TO RELATED APPLICATION:

This is a continuation-in-part of U.S. Ser. No. 365,695, filed May 31, 1973, now abandoned.

BACKGROUND OF THE INVENTION

The present invention relates to a method of preparation of a tin-polyphosphate complex intended to be labelled with 99m Technetium for medical diagnosis by scintigraphy, especially bone scintigraphy.

The invention also relates to a medical diagnosis kit which contains, in a single bottle or flask, the elements to be used in scintigraphy, after labelling thereof.

99m Technetium is endowed with properties which are highly looked for in the medical field, in particular as regards bone scintigraphy and the detection of bone cancerous humors.

In addition to the fact that it can readily be obtained from 99 Mo, this substance has a high quality radiation, a $\gamma$-radiation energy of 140 keV and a short half-life of 6 hours with no emission of $\beta$-rays.

Furthermore, said substance makes it possible to associate a highly-accurate diagnosis with an acceptable, easily employed, dose for the patient.

99m Tc is commonly used for examining various organs such as the thyroid gland, the brain, the liver, the splean, the kidvens and the reticulo-endothelial system. To this end, this substance is incorporated into the body in association with a vehicular compound, chosen in view of its tropism and of its particular biological properties.

According to recent researches, it is known to use polyphosphates labelled with 99m Tc in the field of scintigraphy. Some of these polyphosphates, e.g. triphosphate, as well as some polyphosphates having a molecular weight of 4 500 give excellent results, but such is not the case with the diacidic phosphate and with fluorophosphate which are characterized by poor tropism.

The labelling of these substances, is conventionally accomplished by adding to a pertechnetate solution a freshly prepared solution of stannous chloride in a diluted hydrochloric medium, stirring the mixture for 3 to 5 minutes, adding a polyphosphate solution, stirring thoroughly, adjusting the pH to approximately 7.5 by means of a sodium hydroxide or sodium bicarbonate solution, finally sterilizing the preparation by filtering the latter through a 0.22 $\mu$ filtering membrane in a pre-sterilized empty bottle.

Labeling methods of this type have the disadvantages of being complex, of providing a composition which does not keep well and requires at the moment of use a large number of operating steps which, quite often, cannot be readily performed or even cannot be carried out at all, prior to injection into the patient. For instance, freshly prepared stannous chloride is not always available, and the numerous successive operating steps, involving adding reagents, stirring and adjusting pH-values, complicate the preparations which are required for the medical diagnosis procedure.

Moreover, prior researches on the Tc99 labelling of polyphosphates suggested that the effective substances were essentially large molecules having a very high molecular weight (above 1,500), such as mentioned e.g. in G. Subramanian's works (99mTc polyphosphate PP 46 : A new radio-pharmaceutical for skeletal imaging, Upstate Medical Centre, Syracuse N.Y., 16th Session, June 1971). Indeed, whereas monophosphate had provided but poor results, triphosphate had brought a marked improvement since it was better fixed to the bones and more chemically stable. The natural tendency appeared to lead to polyphosphates of high molecular weight, containing many phosphorous atoms in their chain.

On the other hand, the implication was left that pyrophosphate ($P_2O_7Na_4$) might not be used as a valuable vehicular substance for Tc99 at the level of the skeleton, in view of the rapid hydrolysis thereof by pyrophosphatases.

SUMMARY OF THE INVENTION

It has now been found that pyrophosphate is a very good potential vehicular substance for Tc99 in the bone system, and that it provides remarkable results as regards bone scintigraphy. With pyrophosphate, it is possible to carry out bone scintigraphies after a time-period (required by elimination from organs) which is shorter than in the case of polyphosphates. It is, therefore, also possible to operate with smaller activities.

Accordingly, one of the objects of this invention is to provide a method for preparing a tin-pyrophosphate complex, comprising admixing a pyrophosphate solution with a freshly prepared solution of stannous chloride in an acidic medium and at least partially neutralizing the mixture of these two solutions by raising the pH thereof to a value in preferred range of 5 to 7, and, in particular, 6 to 6.5.

DETAILED DESCRIPTION OF THE PREFERRED EMBODIMENTS

Sodium pyrophosphate has the advantage of being easily prepared in a reproducible manner, which leads to both excellent and permanent results.

The tin-pyrophosphate complex can be used in various ways. As indicated above, it is prepared by first mixing a pyrophosphate solution and a stannous chloride solution together and then adjusting the pH of the mixture to a value within the range 5–7, more preferably 6–6.5.

Once the complex is formulated according to a first mode, it is stored as a liquid solution in vacuo or under an inert gas, such as e.g. nitrogen, or argon, and ultimately sold in bottles, or flasks, as a kit so that, at the moment of use, a radioactive labelling, solution containing Tc99 is simply added thereto and mixed with the complex thus enabling it to serve as a basis for bone scintigraphy by intraveneous injection.

According to a second method, the thus-obtained tin-pyrophosphate complex is first lyophilized in vacuo in order to provide a powder which is itself kept, in vacuo or in an inert atmosphere, in a bottle or kit on sale in shops. In order to use such a kit, one merely has to dissolve the bottled powder in a solution of a Tc99-salt, in order to provide an injection for which is ready for an intravenous solution and bone scintigraphy of a patient. Such a salt is preferably sodium pertechnetate.

Of course, these methods are of particular interest to commercial use of the invention since it is possible to have, at the moment of use, a tin-pyrophosphate composition labelled with Tc99. However, in a laboratory provided with both the means necessary for conveniently preparing the tin-pyrophosphate complex, and the Tc99 compound, it might quite obviously be contemplated to prepare said tin-pyrophosphate complex labelled with Tc99 for intravenous injections, directly without requiring the intermediate step of providing the tin-pyrophosphate complex, in the liquid or the powdered form, within a sterilized bottle in an inert atmosphere.

The accurate value of the pH to which the pyrophosphate solution must be brought after its admixture with stannous chloride in an acidic medium is not critical and may vary in a rather wide range, e.g. from 5 to 7. The selection of that accurate value depends upon the stability of the complex to be prepared, said complex being quite stable at pH's between 5 and 7, and upon biological requirements. The optimum value therefore happens to be in the 6 – 6.5 range, which is a fair compromise with favorable biological injection conditions : although blood is in fact a buffered medium, the pH of which has an average value slightly under 7, it is advisable, unless special precautions are taken, not to inject into a patient's vein a solution having a pH too markedly under 6.

A particular object of the invention is to provide a tin-pyrophosphate composition obtained, in particular, according to the above described method, in which the ratio of the molecular concentrations of pyrophosphate and of tin is at least 30. With such ratio, the complex is effectively formed and the solution contains no tin in the colloidal state.

The use, according to the invention, of compound of pyrophosphate and tin of low molecular weight (at least with respect to the high molecular weights recommended in the prior art) has various advantages. In particular it provides a faster elimination by the kidneys, which causes the parasitic image of that organ and also that of the liver to quickly disappear to the benefit of the bones, thus providing faster examination.

Moreover, tests have shown that the tin-pyrophosphate complexes according to the invention sustain hydrolysis fairly well and, when labelled with Tc99, are a very good vehicular agent for the latter substance. This was by no means obvious at first and, at any rate, invalidates the prior art tendency to resort to bigger and bigger molecules for carrying 99mTc to the bones.

An explanatory illustration of the method according to the invention is provided by the following examples.

EXAMPLE 1.

This example relates to the preparation of a tin-pyrophosphate complex in the solution state and labelled with 99mTc.

After having successively introduced into a bottle a solution containing 100 mg of pyrophosphate $P_2O_7Na_4H_2$ in 2 ml of water and a freshly prepared solution of stannous chloride containing 1.2 mg of $SnCl_2, 2H_2O$ in 0.5 N HCl, neutralization was carried out with sodium hydroxide up to a pH of 6.5 ; 5 ml of $NaTcO_4$ in a 9°/$_{oo}$NaCl medium were added, and stirring was carried out for 5 minutes, followed by filtration with a millipore filter in order to ensure sterilization. The efficiency of labelling by paper chromatography in a 85 % methanol-water medium was found to be 90%.

EXAMPLE 2.

In this example, which also relates to the direct preparation of a tin-pyrophosphate complex in the solution state labelled with 99mTc, the operating steps are as in example 1, but the solution is neutralized with sodium hydroxide up to a pH of 5.2.

5 ml of solution of $TcO_4Na$ in a 9% NaCl medium were added, then stirring was carried out for 5 minutes and filtration was performed with a millipore filter in order to ensure sterilization. The efficiency of labelling by paper chromatography in a 85 % methanol-water medium was found to be about 90 %.

EXAMPLE 3.

This example describes the preparation in powder form of the tin-pyrophosphate composition intended to be labelled at a later time with 99m Tc. Two solutions were prepared, viz. a solution A containing 3 g of pyrophosphate $P_2O_7Na_4$, 10 $H_2O$ dissolved in 60 ml of boiled water, and a solution B containing 0.6 g of $SnCl_2$, 2 $H_2O$ in 500 ml 0.5 N HCl prepared in boil water; 30 ml of solution B were added to the whole amount of solution A, the addition being carried out in an inert gas stream while stirring for 5 minutes, neutralization being then carried out by means of 5 N NaOH up to a pH value of 6.3. The thus obtained solution contained approximately 100 ml of $P_2O_7Na_4$, $10H_2O$ and 1.2 mg of $SnCl_2$, 2 $H_2O$ in 3 ml.

3 ml of the solution were distributed into 30 bottles of the penicilline type. These bottles were treated with a lyophilizer in order to provide a powder, and stored with crimped-on caps in a nitrogen atmosphere up to the moment of labelling with 99m TC.

In order to carry out the labelling later on i.e., at the moment of use there was added to the contents of each bottle 5 ml of a Tc $O_4Na$ solution in a 9°/$_{oo}$ NaCl medium, as obtained by eluting the 99 Mo based generator. Stirring was applied for 5 minutes and filtration was carried out with a millipore filter.

Checking of the labelling carried out as in example 1 indicated efficiencies of 97 - 97, 98 - 98.5 and 92 %, for bottles stored during 1, 5, 11, 15 and 19 days, respectively.

EXAMPLE 4.

This example relates to the preparation of tin-pyrophosphate in the liquid form.

Two solutions were prepared, viz. a solution A containing 3 g of $P_2O_7Na_4$ pyrophosphate, 10 $H_2O$ dissolved in 60 ml of boiled water, and a solution B containing 0.6 g of $SnCl_2$, 2 $N_2O$ in 500 ml of 0.5 N HCl prepared in boiled water; 30 ml of solution B were added to the whole amount of solution A, the addition being carried out in an inert gas stream while stirring for 5 minutes, then neutralization with 5 N NaOH was performed up to pH 7.

The thus obtained solution contained about 100 ml of $P_2O_7Na_4$, 10 $H_2O$ and 1.2 mg of $SnCl_2$, 2 $H_2O$ in 3 ml.

3 ml of that solution were distributed into 30 bottles of the penicilline type and kept in an inert atmosphere (e.g. nitrogen or argon) or in vacuo.

In order to carry out the labelling, 5 ml of the $TcO_4Na$ solution in a 9°/$_{oo}$ NaCl medium obtained by eluting the 99 Mo based generator were added to the contents of each bottle, then stirring was carried out for 5 minutes and filtration was performed with a millipore filter.

Checking of the labelling, carried out as in Example 1, indicated efficiencies of 97 - 97, 98 - 98.5 and 92 %, for bottled stored during 1, 5, 11, 15 and 19 days respectively.

EXAMPLE 5.

The operating steps were the same as in example 3, the only difference being that after lyophilizing the 30 bottles of the penicilline type the bottles were kept in vacuo.

The labelling efficiency obtained after having stored the bottles for 1, 5, 11, 15, 19 and 29 days were 91, 94, 95.2, 93.7, 91 and 91 % respectively.

As regards all the labelling steps mentioned in the above example, scintigraphy was performed on rats and provided similar results in all cases.

Clinical results concerning tests carried out with the 99mTc labelled tin-pyrophosphate complex according to the invention on animals, are given hereunder in three tables, in which:

Table I gives the distribution of 99m Tc among various organs of rats, as a percentage of the activity injected, after 15 minutes, 1 hour and 2 hours, respectively.

Table II shows the elimination, through rat's urine, of the same substance, in percentages, after 15 min, 1 hour, 2 hours, 3 hours and 4 hours, respectively.

utes, 1 hour and 2 hours, respectively, following injection.

2. Blood and urine kinetics.

The method used for blood clearance was that of out-of-the-body circulation achieved by means of a catheter inserted into the carotid and passing through a "well" counter. Urine clearance was carried out by counting the total volumes of urine ejected after fixed periods of time of 15 minutes, 30 minutes, 1 hour, 2 hours, 3 hours and 4 hours.

3. Scintigraphy.

The animal was anesthetized with ethylcarbamate after injection and immediately before scintigraphy was carried out. Scintigraphy was carried out after 5 minutes, 1 hour, 2 hours and 4 hours following injection. Two recording methods were applied:

a. conventional scanning,
b. scanning, followed by information treatment for calculating surface activities.

Analysis of results.

The figures given in table I are the average values of the results achieved with 25 animals. The table also

TABLE I

99m Tc distribution in rats, after an injection of 99m Tc labelled pyrophosphate.
The results are given as a percentage of the activity injected

| Organ | 15 minutes | 1 hour | 2 hours |
|---|---|---|---|
| Blood per cm$^3$ | 2.5 ± 0.4 | 1.5 (1 – 1.7) | 1.3 (1.1 – 1.8) |
| Total Amount of urine | 5.5 (4 – 7) | 21 (16 – 24) | 32 (28 – 40) |
| Kidney (per g) | 1.2 (0.78 – 1.5) | 3.8 (0.9 – 5.45) | 1.6 (0.65 – 4.27) |
| Total Amount | 3.3 (2.14 – 4.12) | 10.5 (2.48 – 15.02) | 4.4 (1.79 – 11.17) |
| Bladder (per g) | 0.08 (0.04 – 0.13) | 0.15 (0.05 – 0.24) | 3.1 (1.52 – 6.10) |
| Bones (per g) | 0.61 (0.15 – 1.89) | 1.47 (0.78 – 2.56) | 1.89 (1.45 – 3.58) |
| Liver (per g) | 0.062 (0.025 – 0.12) | 0.071 (0.033 – 0.11) | 0.12 (0.048 – 0.17) |
| Liver (total amount) | 0.745 (0.031 – 1.42) | 0.85 (0.39 – 1.32) | 1.46 (0.575 – 2.04) |
| Spleen (per g) | 0.039 (0.024 – 0.049) | 0.038 (0.024 – 0.058) | 0.027 (0.014 – 0.037) |

TABLE II

Elimination through rat's urine after an injection of labelled pyrophosphate. (Average values obtained after tests carried out on 50 rats. The results are given in % of the total activity eliminated with respect to the total activity injected.)

| 15 minutes | 5.5 % | (4 – 7) |
|---|---|---|
| 1 hour | 18 % | ± 4 |
| 2 hour | 30 % | ± 5 |
| 3 hour | 34 % | ± 5 |
| 4 hour | 37 % | ± 5 |

Experimental method.

1. Distribution of radioactivity.

The distribution of radioactivity for various organs (blood, urine, kidneys, bones, liver and spleen was studied) as a function of time. The animals (rats of the Winster-Saclay stock, having a weight of from 320 to 400 g) underwent an intravenous injection in their tails. The dose varied between 20 and 50 µ Ci of 99m Tc for a constant amount of pyrophosphate by weight. The animals were destroyed after time-periods of 15 minmentions the limit values for a given organ. They are given as percentages of the activity injected, per unit volume or unit weight according to the organ considered.

Some results apply to the whole organ. The activities of soft organs e.g. liver, spleen (1.46 %) is negligible as compared to the activity fixed on bones.

The pharmaco-kinetic study of blood and urine clearances (table II) indicates the biological behaviour of the substance and gives an indication of how quickly it is eliminated. The labelled substance is quickly eliminated from the vascular compartment to the benefit of bone tissues; an important amount (30 % within 2 hours) is to be recuperated in urine, which leads to think that there is a rapid transit at the kidney stage.

Checking of the labelling is performed by paper chromatography. As a matter of fact, such a method merely permits to check the disappearance of pertechnetate in the free state, and not the compound labelling per se. However, since the absence of pertechnetate is a critical requirement for a single step kit and in view of the fact that the method is time-saving and reproducible without special conditions, such method is useful for routine control.

TABLE III

Stability of the tin-pyrophosphate solution kept in single step kits.

| No. of days following the preparation of the kit | complex in the solution (state % TCO$_4$- after labelling) | | | lyophilized complex (%TCO$_4$- after labelling) | | |
|---|---|---|---|---|---|---|
| | 15 min | 2 hours | 24 h | 15min | 2h | 24 h |
| 1 | 0.2 | 0.5 | 0.5 | 0.1 | 0.5 | |
| 8 | 0.5 | | | | | |
| 13 | 0.3 | 0.6 | 0.6 | 0.3 | 0.5 | 0.6 |
| 23 | 0.4 | | | 0.1 | | |
| 40 | 0.8 | 0.6 | 0.5 | 0.1 | 0.1 | |
| 60 | 0.5 | 1.7 | | 0.2 | 0.5 | |

The results mentioned in table III are obtained by means of the above analysis method. It is to be noted that the tinpyrophosphate solution kept in a nitrogen atmosphere is quite stable, since the labelling efficiency shows no decrease after 60 days following preparation, which leads to think that said solution can remain good for much more than 60 days.

On the other hand, it was observed that a similar solution kept sterile in air evolved rapidly by oxidizing; 11, 12, 45 and 91 % of pertechnetate were recuperated after 1, 5, 11 and 15 days, respectively.

Table III gives an indication of how stable the tin-pyrophosphate kit according to the invention is after a period of time of from 1 to 60 days both in the solution form (column 1) and in the lyophilized form (column 2); activity is given in % Tc after time-periods of 15 minutes, 2 hours and 24 hours respectively, following the radioactive labelling.

The percentages provided refer to the non complexed portion of 99 m Tc, and the results are all the better as the figures are smaller. it appears obviously from table III that a kit which was prepared 60 days ago is still quite efficient and that its activity shows no decrease with respect to what it was at the moment of preparation.

Finally, table IV clearly shows the unexpected advantages provided by the pyrophosphate complex as compared to polyphosphate, in the bone scintigraphy examination, carried out 2 hours and 4 hours, respectively, after the intraveneous injection.

TABLE IV

| | 2 hours | | 4 hours | |
|---|---|---|---|---|
| | polyphosphate labelled with 99 m Tc | Pyrophosphate labelled with 99 mTc | | |
| Normal bone/ soft tissues surface activity ratios | 3.67 | 4.9 | 3.83 | 5.83 |
| Normal spine surfacic activity counts (mCi/m$^2$) | 85.5 | 111 | 63.7 | 79.3 |

What is claimed is:

1. A method for preparing a tin-pyrophosphate complex labelled with 99 m Tc and intended for medical diagnosis by scintigraphy, comprising a first step consisting in admixing a pyrophosphate solution with a freshly prepared solution of stannous chloride in an acidic medium, and at least partially neutralizing the solution, and a second step consisting in admixing the thus obtained mixture with a solution containing 99 m Tc, at the moment of use.

2. A method for preparing a tin-pyrophosphate complex labelled with 99 m Tc according to claim 1, wherein neutralization of said solution is achieved by bringing the pH thereof to a value within the range of 5 to 7.

3. A method for preparing a tin-pyrophosphate complex labelled with 99$^m$ Tc according to claim 2, which further comprises lyophilizing said mixture after said increase of the pH at the end of said first step so as to obtain said complex in powder form.

4. A method for preparing a tin-pyrophosphate complex labelled with 99m Tc according to claim 3, wherein, following the lyophilization step, said compound is kept in vacuo.

5. A method for preparing a tin-pyrophosphate complex labelled with 99m Tc according to claim 3, wherein, following the loyphilization step, said compound is kept in an inert nitrogen or argon atmosphere.

6. A method for preparing a tin-pyrophosphate complex according to claim 1, wherein said solution containing 99m Tc is a solution of sodium pertechnetate TcO$_4$Na.

7. A method for preparing a tin-pyrophosphate complex according to claim 1, wherein said pyrophosphate is sodium pyrophosphate.

* * * * *